United States Patent [19]

Wilkinson et al.

[11] 4,423,242
[45] Dec. 27, 1983

[54] PHARMACEUTICAL AMIDES, AND PREPARATION, FORMULATIONS AND USE OF THEREOF

[75] Inventors: Samuel Wilkinson, Beckenham; George W. Hardy, Biggin Hill; Roger Wrigglesworth, Sevenoaks, all of England

[73] Assignee: The Wellcome Foundation Ltd., London, England

[21] Appl. No.: 422,995

[22] Filed: Sep. 24, 1982

[30] Foreign Application Priority Data

Sep. 25, 1981 [GB] United Kingdom ................. 8129055

[51] Int. Cl.[3] ...................... C07F 9/38; C07C 69/612; A61K 31/66; A61K 31/215
[52] U.S. Cl. .................. 560/41; 260/456 A; 260/465 E; 260/502.5 D; 260/940; 260/941; 424/210; 424/211; 560/12; 560/13; 560/16; 560/22; 560/39
[58] Field of Search ................. 260/502.5 G, 502.5 D, 260/940, 941, 465 E, 456 A; 560/12, 13, 16, 22, 39, 41

[56] References Cited

U.S. PATENT DOCUMENTS

| 4,105,689 | 8/1978 | Auer et al. ................... 260/502.5 D |
| 4,154,759 | 5/1979 | Parsons et al. ............... 260/502.5 G |
| 4,168,267 | 9/1979 | Petrillo ........................... 260/941 |
| 4,226,610 | 10/1980 | Takematsu et al. ......... 260/502.5 G |
| 4,272,528 | 6/1981 | Von Esch et al. .......... 260/502.5 G |
| 4,396,772 | 8/1983 | Petrillo, Jr. .................. 260/502.5 D |
| 4,399,287 | 8/1983 | Baillie et al. ................ 260/502.5 G |

Primary Examiner—J. E. Evans
Attorney, Agent, or Firm—Donald Brown

[57] ABSTRACT

Compounds of the general formula

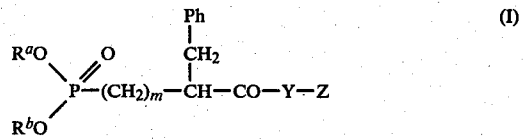

wherein Ph is a phenyl group which is optionally substituted by one or more substituents selected from halo (i.e. fluoro, chloro, bromo or iodo), $C_{1-4}$alkyl, amino, $C_{1-4}$alkylamino, di-$C_{1-4}$alkylamino, nitro, sulphonyl, aminosulphonyl, trihalomethyl, carboxy, $C_{1-4}$alkoxycarbonyl, amido, $C_{1-4}$alkylamido $C_{1-4}$alkoxy, $C_{2-4}$alkenyl, cyano, aminomethyl or methylsulphonyl; $R^a$ and $R^b$, which may be the same or different, each represents a hydrogen or alkali metal (e.g. sodium or lithium) atom or a $C_{1-4}$ (e.g. ethyl) group; m is 0 or 1; Y is a group of formula:

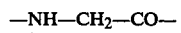

or a group of formula:

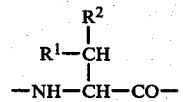

where
$R^1$ is hydrogen or methyl;
$R^2$ is alkyl of 1 to 3 carbon atoms or is methylthiomethyl; and
Z is —$OR^3$ or —$NR_4R^5$ where $R^3$, $R^4$ and $R^5$ are each hydrogen or alkyl of 1 to 4 carbon atoms (i.e. methyl, ethyl, n-propyl, isopropyl, n-butyl, isobutyl, or t-butyl) and $R^3$ can further be phenylalkyl having 1 to 3 carbon atoms in the alkylene moiety thereof, or phenyl; and basic salts thereof. These compounds have an advantageous enkephalinase inhibitory activity which renders the compounds useful in medical therapy, e.g. to prolong and/or potentiate in a mammal, the effects of endogenous or exogenous enkephalins. The latter includes synthetic enkepalin analogues.

19 Claims, No Drawings

PHARMACEUTICAL AMIDES, AND PREPARATION, FORMULATIONS AND USE OF THEREOF

This invention relates to amides and their preparation, to pharmaceutical formulations containing such compounds and the preparation of such formulations, to the use of such compounds in human and veterinary medicine, and to intermediates of value in the preparation of the amides and the preparation of such intermediates.

In 1975, Hughes et al. (Nature Vol. 258, Dec. 18, 1975 pages 577 to 579) identified two related pentapeptides from the mammalian brain with potent opiate agonist activity, the enkephalins;

H.Tyr.Gly.Gly.Phe.Met.OH(Met$^5$-enkephalin)

H.Tyr.Gly.Gly.Phe.Leu.OH(Leu$^5$enkephalin)

(The abbreviations used herein for amino acids and their radicals are those conventional in the art and may be found in, for example, Biochemical Journal (1972) 126, pages 773 to 780. In the above and throughout the following all references are to the L-configuration of chiral amino acids and their radicals unless otherwise stated).

Since the discovery the enkephalins have been studied by a number of workers and from a variety of apporaches. One such approach concerns investigation of their inactivation and recent reports (for example Malfroy et al., Nature Vol. 276, Nov. 30, 1978 pages 523 to 526 and Gorenstein et al., Life Sciences Vol. 25 (1976) pages 2065 to 2070) have indicated that there exists in mammalian brain a dipeptidylcarboxypeptidase ("enkephalinase") capable of hydrolysing the Gly$^3$-Phe$^4$bond H.Tyr.Gly.Gly.Phe.Leu$^{Met}$.OH and thus generating the biologically inactive N-terminal tripeptide fragment H.Tyr.Gly.Gly.OH Enkephalinase thus has or may have a role in some ways comparable with that of the mammalian angiotensin converting enzyme (ACE, EC 3.4.15.1) which acts upon the relatively inactive decapeptide angiotensin I H.Asp.Arg.Val.Tyr.$Ile^{Val}$.His.Pro.Phe.His.Leu.OH at the Phe$^8$-His$^9$ bond to release the potent pressor octapeptide angiotensin II H.Asp.Arg.Val.Tyr.$Ile^{Val}$.His.Pro.Phe.OH although it has been demonstrated (Swerts et al., European Journal of Pharmacology Vol. 57 (1979) pages 279 to 281) that the two enzymes are distinct species.

Controlling the liberation of angiotensin II from angiotensin I, by selectively inhibiting ACE, has for some time been regarded as a possible method for the therapy of hypertension and a number of agents, originating from such an approach and exhibiting the desired properties, have been described. One especially potent compound is 1-(D-3-mercapto-2-methylpropanoyl)-L-proline (S,S), otherwise known as captopril or SQ 14 225 and having the structure

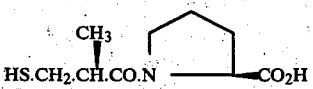

This has been reported as capable of inhibiting both enkephalinase and ACE (Swerts et al., loc.cit.) but as having a far greater specificity for the latter enzyme than for the former, the concentration of compound required to inhibit ACE by 50% being approximately 1000-fold lower than required to effect the same degree of inhibition of enkephalinase.

Published European Patent Application EP 0 038 758 A1 (Roques, Schwartz and Lecomte) describes amino-acid derivatives, said to be capable of inhibiting enkephalinase, in particular, there is disclosed, a compound 'Thirophan' which has the formula

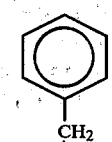

HS—CH$_2$—CH—CO—NH—CH$_2$—CO$_2$H (DL-3-mercapto-2-benzylpropanoyl)-glycine.

The present invention relates to a class of compounds which have not only an advantageous enkephalinase inhibitory activity but also, in distinction to SQ 14 225, a greater specificity for enkephalinase than for ACE.

The present invention thus provides the amides of formula (I):

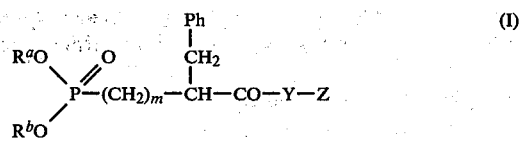

together with basic salts thereof (i.e. salts formed by reaction of a compound of formula (I) with a base), wherein Ph is a phenyl group which is optionally substituted by one or more substituents selected from halo (i.e. fluoro, chloro, bromo or iodo), $C_{1-4}$alkyl, amino, $C_{1-4}$alkylamino, di-$C_{1-4}$alkylamino, nitro, sulphonyl, aminosulphonyl, trihalomethyl, carboxyl, $C_{1-4}$alkoxycarbonyl, amido $C_{1-4}$alkylamido, $C_{1-4}$alkoxy, $C_{2-4}$alkenyl, cyano, aminomethyl or methylsulphonyl; $R^a$ and $R^b$, which may be the same or different, each represents a hydrogen or alkali metal (e.g. sodium or lithium) atom or a $C_{1-4}$ alkyl (e.g. ethyl) group; m is 0 or 1; Y is a group of formula:

—NH—CH$_2$—CO— or a group of formula:

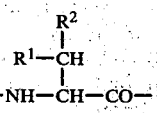

where
R$^1$ is hydrogen or methyl;

$R^2$ is alkyl of 1 to 3 carbon atoms or is methylthiomethyl; and

Z is —$OR^3$ or —$NR^4R^5$ where $R^3$, $R^4$ and $R^5$ are each hydrogen or alkyl of 1 to 4 carbon atoms (i.e. methyl, ethyl, n-propyl, isopropyl, n-butyl, isobutyl, or t-butyl) and $R^3$ can further be phenylalkyl having 1 to 3 carbon atoms in the alkylene moiety thereof or phenyl.

Formula (I) as above includes a plurality of asymmetric centres and should be understood to include all optical isomers embraced thereby and mixtures thereof.

In the salts of the amides of formula (I) the pharmacological activity resides in the amide (acid) anion and the identity of the cation is of less importance although for therapeutic purposes it is preferably pharmacologically and pharmaceutically acceptable to the recipient. Acceptable salts include ammonium salts, alkali metal salts such as lithium, sodium and potassium salts, alkaline earth metal salts such as magnesium and calcium salts, and salts of organic bases, for example amine salts derived from mono-, di- or trilower alkylamines or cycloalkylamines such as dicyclohexylamine or alkanoylamines such triethanolamine and diethylaminoethylamine and salts with heterocyclic amines such as pipiridine, pyridine, piperazine and morpholine.

As subclasses of the amides of formula (I), may be mentioned, (including any appropriate combination thereof) those lised below, as well as processes for their preparation, formulations containing them, methods of treatment (eg of a mammal) by their administration, or said amides for use in prophylaxis and/or treatment of a mammal. Such processes, formulations, methods of treatment and uses, may for example, be any of those described hereinafter. These subclasses are those of the amides of formula (I) wherein:

(i) Ph is unsubstituted phenyl or phenyl substituted by iso-propyl, methoxy, nitro or bromo, in particular in the 4-position;

(ii) Y is a group of formula

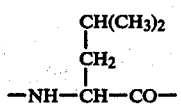

(in either the D- or the L-configuration);

(iii) Y is a group of formula

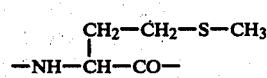

(in either the D- or the L-configuration);

(iv) Y is a group —NH—$CH_2$—CO—;

(v) R is an ethyl, methyl, n-propyl, isopropyl, n-butyl, isobutyl or t-butyl group, in particular a methyl, ethyl or t-butyl group;

(vi) R is hydrogen; and (vii) one or both of $R^a$ and $R^b$ is an alkali metal, independently selected from sodium and lithium.

The amides of formula (I) and their basic salts may be prepared by any of the methods known in the art for the preparation of compounds of analogous structure. Thus they may be prepared by reacting a compound of formula

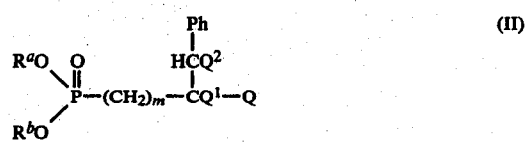

(wherein
$R^a$, $R^b$, m and Ph are as defined in formula (I);
Q is carboxy or a functional equivalent thereof; and
$Q^1$ and $Q^2$ are both hydrogen or together form a bond) with a compound of formula

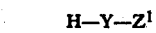

(wherein Y is as defined in formula (I) and $Z^1$ is a group Z as defined in formula (I) or a functionally protected derivative thereof) followed (when $Q^1$ and $Q^2$ together form a bond) by selective reduction of the said bond and, as appropriate, by deprotection of the product and conversion of the product into the amide or a basic salt thereof.

The reaction of (II) with (III) may be effected using techniques standard in peptide chemistry and using either classical methods of peptide synthesis or solid phase procedures. Details of suitable activating and protecting groups and of suitable reaction conditions (both for the reaction of (II) with (III) and for the removal of protecting groups) may be found in the following literature which is given purely by way of exemplification and which is intended to be neither exhaustive nor limiting:

(a) Schroder and Luebke, *The Peptides* (Academic Press) (1965).

(b) Bellean and Malek, *J.Am.Chem.Soc.*, 90, 165 (1968).

(c) Tilak, *Tetrahedron Letters*, 849 (1970).

(d) Beyerman, *Helv.Chim.Acta.*, 56, 1729 (1973).

(e) Stewart and Young, *Solid Phase Peptide Synthesis* (W. H. Freeman and Co.) (1969).

Certain of the amides of formula (I) may also be prepared from precursors which are themselves within formula (I). Thus, (i) compounds wherein Z is —$OR^3$ where $R^3$ is hydrogen may be prepared by hydrolysis of corresponding compounds where $R^3$ is alkyl, phenylalkyl or phenyl;

(ii) compounds wherein Z is —$OR^3$ where $R^3$ is alkyl, phenylalkyl or phenyl may be prepared by esterification of the corresponding compound where $R^3$ is hydrogen;

(iii) compounds wherein Z is —$NR^4R^5$ may be prepared by reaction of a corresponding compound wherein Z is —$OR^3$ where $R^3$ is alkyl, phenylalkyl or phenyl with as appropriate ammonia or a mono- or dialkylamine;

The amides of formula (I) may be converted into basic salts thereof, and the converse, by well established techniques.

Those compounds of formula (II) wherein m is 0 may be prepared for example by reacting a compound of formula.

(wherein $R^a$, $R^b$ and Q are as defined in formula (II)) with a compound of formula.

 (V)

(wherein Ph is as defined in formula (II) and Hal is halo eg. bromo) followed by deprotection as desired to obtain the required compound of formula (II).

Those compounds of formula (II) wherein m is 1 may be prepared for example by reacting a compound of formula

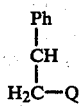 (V)

(wherein Ph and Q are as defined in formula (I)) with an appropriate phosphite of formula

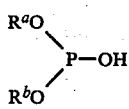

The compounds of formula (V) may be prepared for example from a compound of formula:

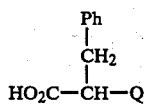 (VI)

(wherein Ph and Q are as defined in formula (I)) according to the procedure of C. Mannich and K. Risert Ber. (1924), 57, 1116.

When the preparative procedures hereinabove described provide a mixture of optical isomers of the amide of formula (I) or of an intermediate thereto, for example a mixture of diastereoisomers, the individual isomers may be separated by appropriate conventional physical techniques such as high performance liquid chromatography, preparative thin layer chromatography and the like.

Because of their selective enkephalinase-inhibiting activity the amides of formula (I) and the basic salts thereof are of value in the in vitro and in vivo investigation of the mode of action and the role of the enzyme and in its localization, isolation and purification.

For example, the present invention provides a method which comprises contacting an amide of formula (I) or a basic salt thereof with enkephalinase and determining the inhibitory effect of the amide or salt on the enzyme activity of the enkephalinase. This method can be used to compare the enkephalinase inhibitory effect of the above compounds with other compounds having a similar effect. The compounds according to the invention can be radiolabelled, if desired, to facilitate the determination of their inhibitory effect.

Their selective enkephalinase-inhibiting activity also confers on the amides of formula (I) and the pharmacologically and pharmaceutically acceptable basic salts thereof utility in the prolongation and/or potentiation in a mammal of the effects of enkephalins of either endogenous or exogenous origin including in the later case synthetic enkephalin analogues. The said amides and salts thus have the same activities and utilities as have been indicated for the endogenous compounds.

The amides of formula (I) may therefore be useful for the prophylaxis and/or treatment of anxiety in mammals such as man, e.g. by virtue of an ability to induce tranquillisation.

The amides of formula (I) may also be useful for the prophylaxis and/or treatment of convulsions in mammals such as man.

A recent study (G. E. Sander et al, Peptides Vol. 2 (1981) pp 403-407) has suggested a role for enkephalins in cardio-pulmonary function. The amides of formula (I) may therefore also be useful for the treatment and/or prophylaxis of a condition of a mammal such as man, wherein an improvement in cardio-pulmonary function is indicated, for example to relieve dyspnoea, e.g. that of acute left ventricular failure or pulmonary oedema.

Furthermore, the amides of formula (I) and the pharmacologically and pharmaceutically acceptable basic salts thereof have morphinomimetic (morphine agonist) activity and thus may be used in the treatment of mammals in the fields of both human and veterinary medicine in any condition where an agent with a morphine-like effect is indicated.

The pharmacological properties and therapeutic uses of morphine are well documented in the literature (see for example The Pharmacological Basis of Therapeutics, Goodman, L S and Gilman, A eds., published by Macmillan Publishing Co., Inc., New York, fifth edition (1975), ISBN 0-02-344781-8, especially Chapter 15 pages 245 to 283, and Martindale: The Extra Pharmacopoeia, Wade, A ed., published by The Pharmaceutical Press, London, twenty-seventh edition (1977), ISBN 0-85369-114-2, especially at pages 970 to 974) and specific utilities for the said amides and salts include, by way of example, the following.

(1) The relief of pain (analgesia), for example pain arising from spasm of smooth muscle as in renal or biliary colic, pain in terminal illness such as terminal cancer, pain in the postoperative period, and obstetrical pain.

(2) The induction of constipation, for example after ileostomy or colostomy.

(3) The treatment of diarrhoea or dysentery.

(4) The suppression of cough.

(5) The induction of sleep, especially where sleeplessness is due to pain or cough.

(6) Sedation, for example in pre-anaesthetic medication to reduce preoperative apprehension.

(7) The induction of euphoria and the treatment of depression, for example when allied to the relief of pain in terminal illness such as terminal cancer.

The amides of formula (I) and the pharmacologically and pharmaceutically acceptable basic salts thereof (hereafter collectively referred to as the active ingredients) may be administered to the human or non-human recipient by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with for example the condition of the recipient.

For each of the above indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable, effective dose will be in the range 0.075 μg to 12 mg per kilogram bodyweight per day, preferably in the range 0.75 μg to 1.2 mg per kilogram bodyweight and most preferably in the range 7.5 to 120 μg per kilogram bodyweight per day, an optimum dose is 30 μg per kilogram bodyweight per day. (Unless otherwise indicated all weights of active ingredient are calculated as the amide of formula (I): for salts thereof the figures would be increased proportionately). The desired dose is preferably presented as between two and four sub-doses administered at appropriate intervals throughout the day. Thus where three sub-doses are employed each will generally lie in the range 0.025 μg to 4 mg, preferably 0.25 μg to 40 μg per kilogram bodyweight with an optimum of 10 μg per kilogram bodyweight. A daily dose for a human weighing of the order of 50 kg will thus generally lie in the range 3.75 μg to 600 mg, preferably in the range 37.5 mg to 60 mg and most preferably 0.375 to 6.0 mg and may conveniently be presented as three equal unit subdoses of 1.25 μg to 200 mg, preferably 12.5 μg to 20 mg and most preferably 0.125 to 2.0 mg. Optimally a human daily dose, for an individual weighing of the order of 50 kg, is 1.5 mg conveniently presented as three unit sub-doses each of 0.5 mg.

While it is possible for the active ingredients to be administered as the raw chemical it is preferable to present them as a pharmaceutical formulation preparation. The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal intrathecal and epidural) administration. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface acctive or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for rectal administration may be presented as a suppository with the usual carriers such as cocoa butter.

Formulations suitable for nasal administration wherein the carrier is a solid include a coarse powder having a particle size for example in the range 20 to 500 microns which is administered in the manner in which snuff is taken, i.e. by rapid inhalation thrugh the nasal passage from a container of the powder held close up to the nose. Suitable formulations wherein the carrier is a liquid, for administration as for example a nasal spray or as nasal drops, include aqueous or oily solutions of the active ingredient.

Formulations suitable for topical administration in the mouth include lozenges comprising the active ingredient in a flavoured basis, usually sucrose and acacia or tragacanth; and pastilles comprising the active ingredient in an inert basis such as gelatin and glycerin, or sucrose and acacia.

Formulations suitable for vaginal administration may be presented as pessaries, creams, pastes or spray formulations containing in addition to the active ingredient such carriers as known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspension which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as hereinabove recited, or an appropriate fraction thereof, of an active ingredient.

It should be understood that in addition to the ingredients particularly mentioned above the formulation of this invention may include other agents conventional in the art having regard to the type of formulation in question, for example those suitable for oral administration may include flavouring agents.

All references id entified hereinabove or in the following are hereby incorporated herein by reference thereto.

Those basic salts which are not pharmacologically and pharmaceutically acceptable may be converted to the amides themselves and to salts thereof which are acceptable by standard procedures.

It will be understood from the foregoing description that this invention may comprise any novel feature described herein, principally but not exclusively for example:

(a) Amides of formula (I) as hereinbefore defined and the basic salts thereof.

(b) Methods as hereinbefore described for the preparation of compounds according to (a) supra, together with the compounds when so prepared.

(c) A pharmaceutical formulation comprising a therapeutically effective amount of an amide of formula (I) as hereinbefore defined or a pharmacologically and pharmaceutically acceptable basic salt thereof together with an acceptable carrier therefor.

(d) A method for the preparation of a formulation according to (c) supra comprising admixture of the active ingredient, as defined, with the carrier therefor.

(e) Amides of formula (I) as hereinbefore defined and pharmacologically and pharmaceutically acceptable basic salts thereof, for use in the therapeutic treatment of a mammal.

(f) Amides of formula (I) as hereinbefore defined and pharmacologically and pharmaceutically acceptable basic salts thereof, for use in the therapeutic treatment of a human.

(g) Amides of formula (I) as hereinbefore defined and pharmacologically and pharmaceutically acceptable basic salts thereof, for use in prolongation and/or potentiation in a mammal of the effects of endogenous or exogenous enkephalins.

(h) Amides of formula (I) as hereinbefore defined, and pharmacologically and pharmaceutically acceptable basic salts thereof, for use in the prophylaxis and/or treatment of anxiety in a mammal such as man.

(i) Amides of formula (I) as hereinbefore defined, and pharmacologically and pharmaceutically acceptable basic salts thereof, for use in the prophylaxis and/or treatment of convulsions in a mammal such as man.

(j) Amides of formula (I) as hereinbefore defined and pharmacologically and pharmaceutically acceptable basic salts therof, for use in the prophylaxis and/or treatment of a condition of a mammal such as man, where an improvement in cardio-pulmonary function is indicated.

(k) Amides of formula (I) as hereinbefore defined and pharmacologically and pharmaceutically acceptable basic salts thereof, for use in the relief of dyspnoea in a mammal such as man, e.g. that of acute left ventricular failure or pulmonary oedema.

(l) Amides of formula (I) as hereinbefore defined and pharmacologically and pharmaceutically acceptable basic salts thereof, for use in the treatment of a mammal for a condition where an agent with a morphine-like effect is indicated.

(m) Amides of formula (I) as hereinbefore defined and pharmacologically and pharmaceutically acceptable basic salts thereof, for use in the treatment of a mammal for a condition selected from those specifically identified hereinabove under (1), (2), (3), (4), (5), (6) or (7).

(n) A method for the prolongation and/or potentiation in a mammal of the effects of endogenous or exogenous enkephalins comprising administration of the mammal of a non-toxic, therapeutically effective amount of an amide of formula (I) as hereinbefore defined or a pharmacologically and pharmaceutically acceptable basic salt thereof.

(o) A method of prophylaxis and/or treatment of anxiety in a mammal, comprising administration to the mammal of a non-toxic, therapeutically effective amount of an amide of formula (I) as hereinbefore defined or a pharmacologically and pharmaceutically acceptable basic salt thereof.

(p) A method of prophylaxis and/or treatment of convulsions in a mammal, comprising administration to the mammal of a non-toxic, therapeutically effective amount of an amide of formula (I) as hereinbefore defined or a pharmacologically and pharmaceutically acceptable basic salt thereof.

(q) A method of prophylaxis and/or treatment of a mammal for a condition where an improvement in cardio-pulmonary function is indicated, comprising administration to the mammal of a non-toxic, therapeutically effective amount of an amide of formula (I) as hereinbefore defined or a pharmacologically and pharmaceutically acceptable basic salt thereof.

(r) A method for the relief of dyspnoea (e.g. that of acute left ventricular failure or pulmonary oedema) in a mammal, comprising administration to the mammal of a non-toxic, therapeutically effective amount of an amide of formula (I) as hereinbefore defined or a pharmacologically and pharmaceutically acceptable basic salt thereof.

(s) A method for the treatment of a mammal for a condition where an agent with a morphine-like effect is indicated comprising administration to the mammal of a non-toxic, therapeutically effective amount of an amide of formula (I) as hereinbefore defined or a pharmacologically and pharmaceutically acceptable basic salt thereof.

(t) A method for the treatment of a mammal for a condition selected from those specifically identified hereinabove under (1), (2), (3), (4), (5), (6) or (7). comprising administration to the mammal of a non-toxic, therapeutically effective amount of an amide of formula (I) as hereinbefore defined or a pharmacologically and pharmaceutically acceptable basic salt thereof.

(u) A method according to (n), (o) (p), (q), (r), (s) or (t) supra wherein the mammal is man.

The following Examples are provided in illustration of the present invention and should not be construed as in any way constituting a limitation thereof. All temperature are in degrees Celsius.

Abbreviations

DMSO = dimethylsulphoxide
DCHA = dicyclohexylamine
THF = tetrahydrofuran
NMM = N-methylmorpholine
DMF = dimethylformamide
TMSiBr = trimethylsilylbromide
TFA = trifluoroacetic acid
DCCl = dicyclohexylcarbodiimide
DCU = dicyclohexyl urea
CA = citric acid

EXAMPLE 1

N-[2-(Dihydroxyphosphinyl)-3-(4-methoxyphenyl)propionyl]-L-leucine (Compound No. 1)

(a)
2-(Diethoxyphosphinyl)-3-(4-methoxyphenyl)propionic acid, ethyl ester

Triethyl phosphonoacetate (53.65 g) was added dropwise with stirring at 20°–25° C. to a suspension of sodium hydride, 50% dispersion in mineral oil (11.47 g) in DMSO. After the evolution of hydrogen had ceased (ca 0.5 hr) a solution of p-methoxybenzyl bromide (48.10 g) in DMSO (50 ml) was added dropwise with stirring. After standing overnight the mixture was heated on the steam bath for 0.5 hr to give a clear solution. The product was poured onto ice water (2 l) and exhaustively extracted with ether. The combined extracts were washed with water, dried (MgSO4) and evaporated to an oil. Distillation gave a fraction b.p. 160°-175°/0.06 mm assigned the correct structure by NMR.

(b) 2-(Diethoxyphosphinyl)-3-(4-methoxyphenyl)propionic acid

The product of stage (a) (10 g) was stirred for 4 hr with 1 M lithium hydroxide (30.5 ml). The mixture was extracted with ether, the aqueous phase cooled to 0° C. and acidified to pH 1.0 with 2 N.HCl and extracted with ethyl acetate, exhaustively. The extracts were dried after washing with brine to give a solid residue. The solid was dissolved in a mixture of ether (35 ml) and ethylacetate (35 ml) and DCHA (4.37 g) added. After refrigeration, the precipitated DCHA salt (m.p. 136°-140°) was filtered and washed with ether. The salt was partitioned between ethyl acetate and 5% citric acid solution, the ethyl acetate extract washed with brine and evaporated in vacuo to give the desired product as a crystalline solid m.p. 94°-98° C.

$C_{14}H_{21}O_6P$ requires: C,53.16, H, 6.69, found: C,53.54, H, 6.50%.

(c) N-[2-(Diethoxyphosphinyl)-3-(4-methoxyphenyl) propionyl]-L-leucine, tert-butyl ester The product of stage (b) was dissolved in THF (20 ml), cooled to −25° C. and with stirring NMM (1.28 g) and then isobutylchloroformate (1.65 g) successively added. After two minutes, a precooled solution of leucine tert-butyl ester (2.15 g) in DMF (5 ml) was added and the mixture stirred at −15° C. for 2 hr. The temperature was raised to 0° C. and stirring continued for 0.5 hr after the addition of 2 M KHCO3 (14 ml). The product was evaporated in vacuo, the residue suspended in ethyl acetate and succesively washed with 5% citric acid, 10% NaHCO3 and brine, dried (MgSO4) and concentrated to a white solid, m.p. 80°-87° (dec). The structure was confirmed by NMR and the product was used in the next stage without further purification.

(d) N-[2-(Dihydroxyphosphinyl)-3-(4-methoxyphenyl)propionyl]-L-leucine

The solid from stage (c) (4 g) was stirred at ambient temperature under a positive pressure of nitrogen for 18 hrs with TMSiBr (4 ml). The product was evaporated in vacuo and then re-evaporated twice with water. The residue was stirred for 6.5 hr with TFA (50 ml), concentrated in vacuo and re-evaporated several times with CCl4. The residue was dissolved in warm 5% NaHCO3 solution, acidified with 2 N.HCl and refrigerated. The white crystalline solid was filtered and dried to give the desired compound as the monosodium salt, m.p. 240°-245°. High resolution NMR confirmed the structure and indicated that the product was a mixture of diastereoisomers in the ration of 1:1

$C_{15}H_{23}NNaO_7P,1.5H_2O$ requires: C, 45.50; H, 6.21; N, 3.32, found: C,45.58; H, 6.06; N, 3.18%.

EXAMPLE 2

N-[2-(Dihydroxyphosphinyl)-3-phenylpropionyl]-L-leucine (a) 2-(Diethoxyphosphinyl)-3-phenylpropionic acid 2-(Diethoxyphosphinyl)-3-phenylpropionic acid ethyl ester b.p. 132°-146°/0.07 mm was prepared from benzylbromide and triethylphosphonoacetate as described for the 4-methoxyphenyl analogue in Example 1 above. Saponification with LiOH gave 2-diethoxyphosphinyl-3-phenylpropionic acid, m.p. 76° C. (from chloroform/light petroleum).

$C_{13}H_{19}O_5P$ requires: C 54.54, H 6.65, found: C 54.56, H 6.64%.

(b) N-[2-(Diethoxyphosphinyl)-3-phenylpropionyl]-L-leucine ethyl ester

To a solution of leucine ethyl ester (3.28 g) and the product of stage (a) (5.72 g) in $CH_2Cl_2$ (30 ml) cooled to −20° C. was added DCCI (4.53 g) and the mixture then stirred at +4° C. for 12 hr. The DCU was filtered and the filtrate concentrated in vacuo to a sticky white solid. This was dissolved in ether, refrigerated and the crystalline solid filtered and recrystallised from ether (isomeric mixture A-compound no. 2), m.p. 86°-87° C.

NMR indicated a diastereoisomeric composition of 3:1.

TLC (Ethyl acetate/n-hexane 1:1) Rf 0.2 and 0.15 with a preponderance of component Rf0.2

$C_{21}H_{34}NO_6P$ requires: C, 59.0; H, 8.0; N, 3.3, found: C, 59.1; H, 8.18; N,3.32%.

The mother liquors after removal of the solid A gave a crop of an isomeric mixture (mixture B- compound no. 3) having a preponderance of the isomer Rf 0.15 (Found: C, 59.1; H, 7.89; N, 3.10%). The two mixtures, having different proportions of the diastereoisomers were processed further independently.

(c) N-[2-(Dihydroxyphosphinyl)-3-phenylpropionyl.-L-leucine] ethyl ester (i) The isomeric mixture A from stage (b) (0.97 g) was stirred with TMSiBr (1.2 ml) under nitrogen for 12 hr. The product was evaporated in vacuo to a viscous oil which solidified on trituration with water. The solid was dried to give a slightly hygroscopic solid (compound no. 4) m.p. 148° C. (0.318 g).

$C_{17}H_{26}NO_6P,0.5H_2O$ requires: C, 53.7; H, 7.1.; N, 3.7, found: C, 53.97; H, 6.92; N, 3.72%.

(ii) similarly the isomeric mixture B from stage (b) (0.3 g) yielded 0.2 g of a product (compound no. 5) m.p. 123°-125°.

$C_{17}H_{26}NO_6P,0.25H_2O$ requires: C, 54.32; H, 7.06; N, 3.73, found: C, 54.25; H, 7.32; N, 3.86%.

(d) N-[2-(Dihydroxyphosphinyl)-3-phenylpropionyl]-L-leucine tri-lithium salt (i) The product from stage (c)(i) above (0.198 g) was suspended in water (1.5 ml) and saponified with 1 M LiOH, maintaining the pH at 11.5 with a pH stat. After 48 hrs, the product which precipitated as the tri-lithium salt was filtered and dried in vacuo (0.095 g) (Compound no. 6).

$C_{15}H_{19}NO_6PLi_31.0H_2O$ requires: C,47.5; H, 5.55; N, 3.60, found: C, 47.12; H, 5.39; N, 3.60%.

(ii) The product from stage (c)(ii) above was saponified in similar manner to give (0.05 g) as the tri-lithium salt (Compound No. 7).

$C_{15}H_{19}NO_6PLi_30.5H_2O$ requires: C, 48.64; H, 5.41; N, 3.78, found: C, 48.60; H, 5.68; N,4.11%.

(e)
N-[2-(Diethoxyphosphinyl)-3-phenylpropionyl]-L-leucine (Compound no.8)

A sample of isomeric mixture A obtained in stage (b) above (0.427 g) suspended in water (1.5 ml) was saponified with 1 M LiOH (2.0 ml) at pH 11.5 (pH stat) for 12 hr. The mixture was filtered and the filtrate concentrated in vacuo to a white solid, which was dissolved in water and acidified to pH 2.5 with CHCl. The precipitated solid was filtered and dried in vacuo to give the above compound m.p. 162°-163° C.

$C_{19}H_{30}NO_6P$ requires: C, 57.1; H, 7.5; N, 3.5, found: C, 56.89; H, 7.78; N, 3.48%.

In an analogous sequence of reactions to those described in Example 1 and 2, the following two compounds were prepared:

Compound No. 9: N-[3-(4-bromophenyl)-2-dihydroxyphosphinylpropionyl]-L-leucine, monosodium salt.

$C_{15}H_{20}BrNNaO_6P$ requires: C 40.56; H 4.54; N 3.15, found: C 40.49; H 4.82; N 2.74%.

Compound No. 10: N-[2-dihydroxyphosphinyl-3-(4-isopropylphenyl)propionyl]-L-leucine, disodium salt.

$C_{18}H_{25}NNa_2O_6P1.5H_2O$ requires: C 47.37; H 6.40; N 3.07, found: C 47.50; H 6.62; N 2.61%.

EXAMPLE 3

N-[2-Benzyl-3-(dihydroxyphosphinyl)propionyl]-L-leucine (a) 2-Benzyl-3-(diethoxyphosphinyl)propionic acid ethyl ester To a mixture of diethylphosphite (6.9 g) and 2-benzylacrylic acid ethyl ester (9.5 g) (prepared according to the procedure of C. Mannich and K. Risert Ber. (1924), 57, 1116 from benzylmalonic acid mono ethyl ester) was added, with stirring at ambient temperature under an atmosphere of nitrogen, a solution of sodium (1.15 g) in ethanol (20 ml). Following the initial exothermic reaction stirring was continued for 48 hr. The solvent was evaporated in vacuo and the residual gum partitioned between ether (100 ml) and 5% CA (50 ml). The ether solution was shaken once more with 5% CA (50 ml), dried (MgSO₄) and the residue distilled, collecting the fraction (3.7 g) m.p. 58°-72°/0.02-0.03 mm). The structure of the product was confirmed by NMR and Mass spectroscopy.

(b) 2-Benzyl-3-(diethoxyphosphinyl)propionic acid

The ester from stage (a) (3.28 g) was saponified at pH 11.3 (pH stat) for 4 hr with 1 N. NaOH (10 ml). The reaction mixture was extracted with ether (30 ml), the aqueous phase acidified to pH 2.0 with ᶜHCl and extracted with ethyl acetate (3×30 ml). The combined extracts were dried (MgSO₄) and evaporated in vacuo to a viscous oil (2.7 g). The structure was confirmed by NMR.

(c)
N-[2-Benzyl-3-(diethoxyphosphinyl)propionyl]-L-leucine ethyl ester

To a solution of leucine ethyl ester (generated from the hydrochloride, 1.96 g) and the product of stage (b) (3.0 g) in methylene dichloride (25 ml) precooled to −20° C., was added DCCI (2.27 g). The mixture was stirred at +4° C. for 48 hr and the DCU filtered. The filtrate was acid/base washed in the normal manner, dried (MgSO₄) and concentrated in vacuo to give an oil (3.51 g). Tlc (Merck silica gel, CHCl₃[EtOAc, 1]1) shows two spots Rf 0.25 and 0.17.

The diastereoisomeric mixture (1.0 g) was fractionated by chromatography on a dry-packed column of silica gel (Merck Kieselgel 60 40×4 cm), eluting with a mixture of CHCl₃[EtOAc, 7]3 and collecting 70 drop fractions.

(1) fractions 148-180 on evaporation gave a crystalline solid m.p. 64°-65° C. Rf 0.25 (0.202 g) (isomer A).

$C_{22}H_{36}NO_6P$ requires: C, 59.9; H, 8.2; N, 3.2, found: C, 59.7; H, 8.38; 3.13%.

(2) fractions 232-262 on evaporation gave a crystalline solid m.p. 66°-67° C. Rf 0.17 (0.127 g) isomer B).

$C_{22}H_{36}NO_6P$ requires: C, 59.9; H, 8.2; N, 3.2, found: C, 59.69; H, 8.13; N, 3.08%.

Tlc and NMR confirmed that isomers A and B were pure separated diastereoisomers.

(d)
N[(2-Benzyl-3-(dihydroxyphosphinyl)propionyl]leucine ethyl ester (i) Isomer A obtained in stage (c) (88 mg) and TMSiBr (1.0 ml) were stirred together under nitrogen for 16 hrs at ambient temperature. The mixture was evaporated in vacuo, triturated twice with water (2 ml) and the solid (62 mg) filtered and dried in vacuo to give a product (compound no. 11).

$C_{18}H_{28}NO_6P$ requires: C, 56.1; H, 7.3; N, 3.65, found: C, 55.87; H, 7.14; N, 3.39%.

(ii) In similar manner, isomer B obtained in stage (c) (88 mg) yielded a product (compound no. 12) (53 mg).

$C_{18}H_{28}NO_6P0.5H_2O$ requires: C, 54.8; H, 7.36; N, 3.55, found: C, 54.55; H, 7.32; N, 3.38%.

(e)
N-[2-Benzyl-3-(dihydroxyphosphinyl)propionyl]leucine (i) The product obtained in stage (d)(i) (385 mg) was suspended in water and stirred for 48 hrs at ambient temperature with 1 N.NaOH (3 ml). The clear solution was cooled to 0° C. and acidified to pH 1.0 with ᶜHCl and the crystalline solid filtered to give a product (84 mg) m.p. 207°-209° (compound no. 13).

$C_{16}H_{24}NO_6P0.5H_2O$ requires: C, 52.45; H, 6.83; N, 3.82, found: C, 52.67; H, 6.61; N, 3.76%.

(ii) In similar manner the product obtained in stage (d)(ii) (385 mg) gave a product (194 mg), m.p. 209°-210° C. (compound No. 14).

$C_{16}H_{24}NO_6P$ requires: C, 53.8; H, 6.7; N, 3.9, found: C, 53.73; H, 6.85; N, 3.86%.

ACTIVITY IN VITRO

The compounds were investigated for enkephalinase-inhibiting activity using the following method.

Purified enkephalinase Al was obtained according to the following procedure (modification of the method of Gorenstein and Snyder, Life Science, Vol. 25, pages 2065-2070, 1979).

Rats were killed by decapitation and the striata dissected out on ice. The pooled tissues were homogenised in ice-cold Tris/hydrochloric acid buffer (50 mM, pH 7.70, 30 ml per gram of tissue) and centrifuged (50,000 g, 15 mins). The resulting supernatent was discarded and the remaining pellet washed three times. The washed pellet was solubilised by resuspension in half the volume of buffer as before containing 1.0% (v/v) Triton X-100 and incubated at 37° C. for 45 mins. The suspension was then centrifuged at 100,000 g for 60 mins and the solubilised enzymes contained in the supernatant separated by DEAE-cellulose column chromatography. Enkephalinase Al was further purified by Sephacryl S.300 chromatography.

Enkephalinase-inhibiting activity was estimated by the following procedure. 1.75 μl of leucine enkephalin (0.317 mg/ml), 0.5 μl of $^3$H-leucine enkephalin (tyrosyl-3,5-$^3$H Enkephalin (5-L-Leucine), The Radiochemical Centre, Amersham, England) and 5.75 μl of buffer as before were incubated at 30° C. for 10 mins with 2 μl of either a solution of test compound (in either 50% ethanol/0.1 M sodium hydrogen carbonate or distilled water) or solvent alone as control. 10 μl of purified enkephalinase Al at 30° C. were added and incubation then continued for a further 30 mins (total incubation time 40 mins, final leucine enkephalin concentration $5 \times 10^{-5}$ M, final $^3$H-leucine enkephalin concentration 12.5 μCi/ml). At the completion of incubation 3 μl of 0.16 M hydrochloric acid was added and the incubation mixture cooled on ice.

Separation of (a) unchanged $^3$H-leucine enkephalin and (b) $^3$H-Tyr-Gly-Gly-OH ($^3$H-TGG), generated from (a) by enkephalinase Al in the incubation mixture was effected by thin layer chromatography (plastic silica gel plates of 0.1 mm layer chromatography (plastic silica gel plates of 0.1 mm layer thickness, solvent system ethyl acetate: propan-2-ol: 5% (v/v) acetic acid, 2:2:1) using solutions of the cold compounds as carriers. After drying the materials were visualized with ninhydrin and appropriate areas of the plates cut out and placed in scintillation vials containing 50% methanol/0.1 M hydrochloric acid to elute the $^3$H label. Biofluor reagent (10 ml) was then added and the radioactivity determined by liquid scintillation counting.

The $^3$H-TGG generated in the presence of test compound (expressed as a percentage of the control figure) was then calculated and an approximate $IC_{50}$ figure (concentration of test compound required for 50% inhibition of $^3$H-TGG generation) then determined graphically.

For comparison purpose, the $IC_{50}$ figures for Captopril and Thiorphan are also given.

| Compound No. | $IC_{50}(M)$ |
|---|---|
| 1 | $1.8 \times 10^{-6}$ |
| 2 | * |
| 3 | * |
| 4 | $6 \times 10^{-7}$ |
| 5 | $1.5 \times 10^{-6}$ |
| 6 | $1.3 \times 10^{-7}$ |
| 7 | $6.8 \times 10^{-7}$ |
| 8 | * |
| 9 | $6.8 \times 10^{-6}$ |
| 10 | $2.3 \times 10^{-5}$ |
| 11 | $6.8 \times 10^{-7}$ |
| 12 | $1 \times 10^{-4}$ |
| 13 | $1.6 \times 10^{-7}$ |
| 14 | $1.8 \times 10^{-5}$ |
| Captopril | $3 \times 10^{-5}$ |
| Thiorphan | $1.2 \times 10^{-8}$ |

*no effect at $3 \times 10^{-5}$

Pharmaceutical Formulations

The compound of formula (I) employed in the following Examples of pharmaceutical formulations may be any compound of formula (I) defined above or a basic salt thereof.

(A) Tablet Formulation (0.5 mg/tablet)

| Compound of formula (I) | 0.5 mg |
|---|---|
| Maize Starch | 10 mg |
| Polyvinylpyrrolidone | 2 mg |
| Magnesium Stearate | 2 mg |
| Lactose | to 100 mg |

Mix together the compound of formula (I), Lactose and Maize Starch. Granulate with a solution of the Polyvinylpyrrolidone dissolved in eater. Dry the granules, add the Magnesium Sterate and compress to produce tablets, 100 mg per tablet.

(B) Suppository (0.5 mg/product)

| Compound of formula (I) | 25 mg |
|---|---|
| Suppository Base (Massa Esterinum C) | to 100 mg |

Melt the suppository base at 40° C. Gradually incorporate the compound of formula (I) in fine powder form and mix until homogenous. Pour into suitable moulds, 2 g per mould, and allow to set. Massa Esterinum C is a commercially available suppository basee consisting of a mixture of mono, di, and triglycerides of saturated vegetable fatty acids. It is marketed by Henkel International, Dussledorf.

(C) Pessary (0.5 mg/product)

| Compound of formula (I) | 0.5 mg |
|---|---|
| Lactose | 400 mg |
| Polyvinylpyrrolidone | 5 mg |
| Magnesium Stearate | 4.5 mg |

Mix together the compound of formula (I) and Lactose. Granulate with a solution of Polyvinylpyrrolidone in 50% aqueous ethanol. Dry the granules, add the Magnesium Steate and compress on suitable shaped punches, 410 mg per pessary.

(D) Freeze-dried Injection 0.5 ml/vial

| Compound of formula (I) | 0.5 mg |
|---|---|
| Mannitol | 99.5 mg |
| Water for Injections to | 2.0 ml |

Dissolve the compound of formula (I) and mannitol in the Water for Injections. Sterilise the solution by passage through a membrane filter, 0.2 μm pore size, collecting the filtrate in a sterile receiver. Fill into sterile glass vials, 2 ml/vial under aseptic conditions and freeze-dry. Close the vials with sterile rubber closures secured with an aluminium seal.

The injection is reconstituted prior to administration by the addition of a convenient volume of Water for Injections or sterile saline solution.

We claim:
1. Compounds of the general formula

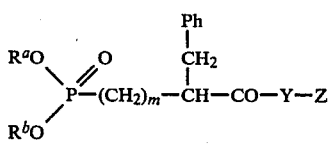

wherein Ph is a phenyl group which is optionally substituted by one or more substituents selected from halo (i.e. fluoro, chloro, bromo or iodo), $C_{1-4}$alkyl, amino, $C_{1-4}$alkylamino, di-$C_{1-4}$alkylamino, nitro, sulphonyl, aminosulphonyl, trihalomethyl, carboxy, $C_{1-4}$alkoxycarbonyl, amido, $C_{1-4}$alkylamido, $C_{1-4}$alkoxy, $C_{2-4}$alkenyl, cyano, aminomethyl or methylsulphonyl; $R^a$ and $R^b$, which may be the same or different, each represents a hydrogen or alkali metal atom or a $C_{1-4}$alkyl group; m is 0 or 1; Y is a group of formula:

or a group of formula:

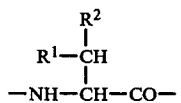

where
$R^1$ is hydrogen or methyl;
$R^2$ is alkyl of 1 to 3 carbon atoms or is methylthiomethyl; and
Z is $-OR^3$ or $-NR^4R^5$ where $R^3$, $R^4$ and $R^5$ are each hydrogen or alkyl of 1 to 4 carbon atoms (ie. methyl, ethyl, n-propyl, isopropyl, n-butyl, isobutyl, or t-butyl) and $R^3$ can further be phenylalkyl having 1 to 3 carbon atoms in the alkylene moiety thereof, or phenyl; and basic salts thereof.

2. Compounds as claimed in claim 1, wherein Ph is unsubstituted phenyl or phenyl substituted by iso-propyl, methoxy, nitro or bromo.

3. Compounds as claimed in claim 2, wherein Ph is phenyl substituted in the 4-position by iso-propyl, methoxy, nitro or bromo.

4. Compounds as claimed in any of claims 1-3, wherein Y is a group of formula

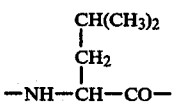

(in either the D- or the L-configuration).

5. Compounds as claimed in any of claims 1-3, wherein Y is a group of formula

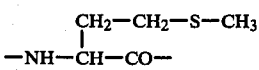

(in either the D- or the L-configuration).

6. Compounds as claimed in any of claims 1-3, wherein Y is a group $-NH-CH_2-CO-$.

7. Compounds as claimed in any of claims 1-3, wherein Z is $-OR^3$, where R is an ethyl, methyl, n-propyl, isopropyl, n-butyl, isobutyl or t-butyl group.

8. Compounds as claimed in any of claims 1-3, wherein Z is $-OR^3$, where R is an ethyl, methyl, or t-butyl group.

9. Compounds as claimed in any of claims 1-3, wherein Z is $-OR^3$, where R is hydrogen.

10. Compounds as claimed in any of claims 1-3, wherein one or both of $R^a$ and $R^b$ is an alkali metal, independently selected from sodium and lithium.

11. N-[2-(dihydroxyphosphinyl)-3-(4-methoxyphenyl)propionyl]-L-leucine and basic salts thereof.

12. Either diastereoisomer (or a mixture in any proportion thereof) of N-[2-(dihydroxyphosphinyl)-3-phenylpropionyl]-L-leucine ethyl ester and basic salts thereof.

13. Either diastereoisomer (or a mixture of any proportion thereof) of N-[2-(dihydroxyphosphinyl)-3-phenylpropionyl]-L-leucine trilithium salt.

14. N-[3-(4-bromophenyl)-2-dihydroxyphosphinylpropionyl]-L-leucine and basic salts thereof.

15. N-[3-(4-bromophenyl)-2-dihydroxyphosphinylpropionyl]-L-leucine monosodium salt.

16. N-[2-dihydroxyphosphinyl-3-(4-isopropylphenyl)propionyl]-L-leucine and basic salts thereof.

17. N-[2-dihydroxyphosphinyl-3-(4-isopropylphenyl)propionyl]-L-leucine disodium salt.

18. Either diastereoisomer (or a mixture in any proportion thereof) of N-[2-benzyl-3-(dihydroxyphosphinyl)propionyl]-L-leucine ethyl ester, and basic salts thereof.

19. Either diastereoisomer (or a mixture in any proportion thereof) of N-[2-benzyl-3-(dihydroxyphosphinyl)propionyl]leucine and basic salts thereof.

* * * * *